(12) United States Patent
Sanchez et al.

(10) Patent No.: US 9,700,387 B2
(45) Date of Patent: Jul. 11, 2017

(54) POROUS IMPLANT

(71) Applicant: Zimmer Dental, Inc., Carlsbad, CA (US)

(72) Inventors: Ramiro Sanchez, Temecula, CA (US); John Zacharia, San Diego, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 15 days.

(21) Appl. No.: 13/912,740

(22) Filed: Jun. 7, 2013

(65) Prior Publication Data

US 2014/0030675 A1    Jan. 30, 2014

Related U.S. Application Data

(60) Provisional application No. 61/675,491, filed on Jul. 25, 2012.

(51) Int. Cl.
| A61C 8/00 | (2006.01) |
| A61C 8/02 | (2006.01) |
| A61K 6/04 | (2006.01) |
| A61L 27/56 | (2006.01) |
| A61L 27/04 | (2006.01) |

(52) U.S. Cl.
CPC ............ *A61C 8/0025* (2013.01); *A61C 8/005* (2013.01); *A61C 8/0006* (2013.01); *A61C 8/0012* (2013.01); *A61C 8/0013* (2013.01); *A61K 6/04* (2013.01); *A61L 27/047* (2013.01); *A61L 27/56* (2013.01); *A61L 2430/12* (2013.01)

(58) Field of Classification Search
CPC ..... A61B 17/863; A61C 8/0012; A61C 8/005; A61C 8/0025; A61C 8/0006; A61C 8/0013; A61K 6/04; A61L 27/047; A61L 27/56; A61L 2430/12
USPC ...................................... 433/172–174, 201.1
See application file for complete search history.

(56) References Cited

U.S. PATENT DOCUMENTS

| 5,282,861 A | | 2/1994 | Kaplan | |
| 5,360,448 A | * | 11/1994 | Thramann | ............ A61B 17/863 |
| | | | | 411/412 |
| 5,989,027 A | | 11/1999 | Wagner et al. | |
| 6,095,817 A | * | 8/2000 | Wagner et al. | ................ 433/173 |

(Continued)

FOREIGN PATENT DOCUMENTS

| FR | 2929102 A1 | 10/2009 | |
| WO | WO 2010002664 A1 | * 1/2010 | ........... A61C 8/0012 |

(Continued)

OTHER PUBLICATIONS

"International Application Serial No. PCT/US2013/044729, International Search Report mailed Aug. 20, 2013", 5 pgs.

(Continued)

*Primary Examiner* — Cris L Rodriguez
*Assistant Examiner* — Mirayda A Aponte
(74) *Attorney, Agent, or Firm* — Schwegman Lundberg & Woessner, P.A.

(57) ABSTRACT

An implant can include a core having a head portion and a stem portion extending from the head portion. The stem portion can include an intermediate threaded section, a first porous section located along the stem portion, and a second porous section located along the stem portion, wherein the intermediate threaded section of the stem separates the first porous section from the second porous section.

25 Claims, 4 Drawing Sheets (56) References Cited

U.S. PATENT DOCUMENTS

| | | |
|---|---|---|
| 7,291,012 B2 | 11/2007 | Lyren |
| 8,075,312 B2 | 12/2011 | Collins et al. |
| 2007/0172796 A1 | 7/2007 | Hyun et al. |
| 2007/0270858 A1* | 11/2007 | Trieu ................ A61B 17/7098 606/279 |
| 2008/0241793 A1* | 10/2008 | Collins et al. ................ 433/174 |
| 2010/0003638 A1* | 1/2010 | Collins et al. ................ 433/174 |
| 2010/0003640 A1* | 1/2010 | Damstra et al. ........... 433/201.1 |
| 2010/0330534 A1* | 12/2010 | Hyun ............................ 433/174 |
| 2012/0156646 A1 | 6/2012 | Pelote |

FOREIGN PATENT DOCUMENTS

| | | |
|---|---|---|
| WO | WO-2010146383 A1 | 12/2010 |
| WO | WO-2014018166 A1 | 1/2014 |

OTHER PUBLICATIONS

"International Application Serial No. PCT/US2013/044729, Written Opinion mailed Aug. 20, 2013", 11 pgs.

"International Application Serial No. PCT/US2013/044729, International Preliminary Report on Patentability mailed Feb. 5, 2015", 13 pgs.

"European Application Serial No. 13731568.5, Communication Pursuant to Article 94(3) EPC mailed Feb. 15, 2017", 5 pgs.

\* cited by examiner

POROUS IMPLANT

CLAIM OF PRIORITY

This application claims the benefit of U.S. Provisional Patent Application Ser. No. 61/675,491, filed on Jul. 25, 2012, the benefit of priority of which is claimed hereby, and is incorporated by reference herein in its entirety.

FIELD

The present subject matter relates to an orthopedic system and specifically to a porous implant.

BACKGROUND

Often it can be desirable to replace lost, missing, injured, or diseased teeth using dental devices. Prosthetic dental devices can include dental implants, which can be inserted into the mandible or maxilla of a patient, and abutments, which can be attached to the implant to serve as a mount for a prosthetic tooth, and provisional and temporary devices, which can be used during the healing process.

The dental implant can be threaded into a bore which can be drilled into the patient's mandible or maxilla at an edentulous site. Over a period of several months, the patient's jaw bone grows around the implant to securely anchor the implant in the surrounding bone, a process known as osseointegration. The implant provides an anchoring member for a dental abutment, which, in turn, provides an interface between the implant and a dental restoration. For example, U.S. Pat. Nos. 5,989,027 and 8,075,312 discuss dental implants.

OVERVIEW

In Example 1, an implant includes a core, having a head portion and a stem portion extending from the head portion, the stem portion including an intermediate threaded section, a first porous section located along the stem portion, and a second porous section located along the stem portion, wherein the intermediate threaded section of the stem separates the first porous section from the second porous section.

In Example 2, the implant of Example 1 optionally includes the first porous section and the second porous section respectively including first and second porous sleeves disposed around the stem portion.

In Example 3, the implant of any of Examples 1 or 2 optionally includes the first porous section having a greater diameter than the second porous section.

In Example 4, the implant of any of Examples 1 through 3 optionally includes the first porous section located toward a coronal end of the implant and the second porous section located toward an apical end of the implant.

In Example 5, the implant of any of Examples 1 through 4 optionally includes a third porous section located along the stem portion.

In Example 6, the implant of Example 5 optionally includes the stem including a second, intermediate threaded section separate from the intermediate threaded section and the second intermediate threaded section separating the third porous section from the second porous section.

In Example 7, the implant of any of Examples 1 through 6 includes the intermediate threaded section being non-porous.

In Example 8, the implant of any of Examples 1 through 7 optionally includes the first porous section including a porous tantalum sleeve disposed around the stem portion and the second porous section including a porous tantalum sleeve disposed around the stem portion.

In Example 9, the implant of any of Examples 1 through 8 optionally includes the stem portion including a first, coronal threaded section, the intermediate threaded section, and a third apical threaded section.

In Example 10, the implant of any of Examples 1 through 9 optionally includes the first porous section and the second porous section respectively including first and second porous metallic sleeves disposed around the stem portion.

In Example 11, the implant of Example 10 optionally includes the first and second porous metallic sleeves including porous tantalum, porous titanium, or porous niobium sleeves.

In Example 12 an implant includes a core, having a head portion, including an abutment interface, and a stem portion, extending from the head portion, the stem portion including a first, coronal threaded section, an intermediate threaded section, and a third, apical threaded section, a first porous metallic sleeve disposed around the stem portion, a second porous metallic sleeve disposed around the stem portion, wherein the intermediate threaded section of the stem portion separates the first porous metallic sleeve from the second porous metallic sleeve, and wherein the first porous metallic sleeve is located toward a coronal end of the implant and the second porous metallic sleeve is located toward an apical end of the implant.

In Example 13, the implant of Example 12 optionally includes the first porous metallic sleeve having a greater diameter than the second porous metallic sleeve.

In Example 14, the implant of any of Examples 12 or 13 optionally includes a third porous metallic sleeve disposed around the stem portion.

In Example 15, the implant of Example 14 optionally includes the stem portion including a second, intermediate threaded section separate from the intermediate threaded section, and wherein the second intermediate threaded section separates the third porous metallic sleeve from the second porous metallic sleeve.

In Example 16, the implant of any of Examples 12 through 15 optionally includes the first, coronal threaded section, the intermediate threaded section, and the third, apical threaded section being non-porous.

In Example 17, the implant of any of Examples 12 through 16 optionally includes the first porous metallic sleeve including a porous tantalum sleeve and the second porous metallic sleeve including a porous tantalum sleeve.

In Example 18, the implant of any of Examples 12 through 17 optionally includes the first, coronal threaded section having a greater diameter than the intermediate threaded section, and the intermediate threaded section having a greater diameter than the third, apical threaded section.

In Example 19, the implant of any of Examples 12 through 18 optionally includes the first and second porous metallic sleeves including porous tantalum, porous titanium, or porous niobium sleeves.

In Example 20a method includes inserting a dental implant into a mouth such that a first threaded apical section contacts an osteotomy wall, further inserting the dental implant such that an apical porous section contacts the osteotomy wall, further inserting the implant such that an intermediate threaded section contacts the osteotomy wall, and further inserting the implant such that a coronal porous section contacts the osteotomy wall.

In Example 21, the method of Example 20 optionally includes the apical porous section having a smaller diameter than the coronal porous section.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
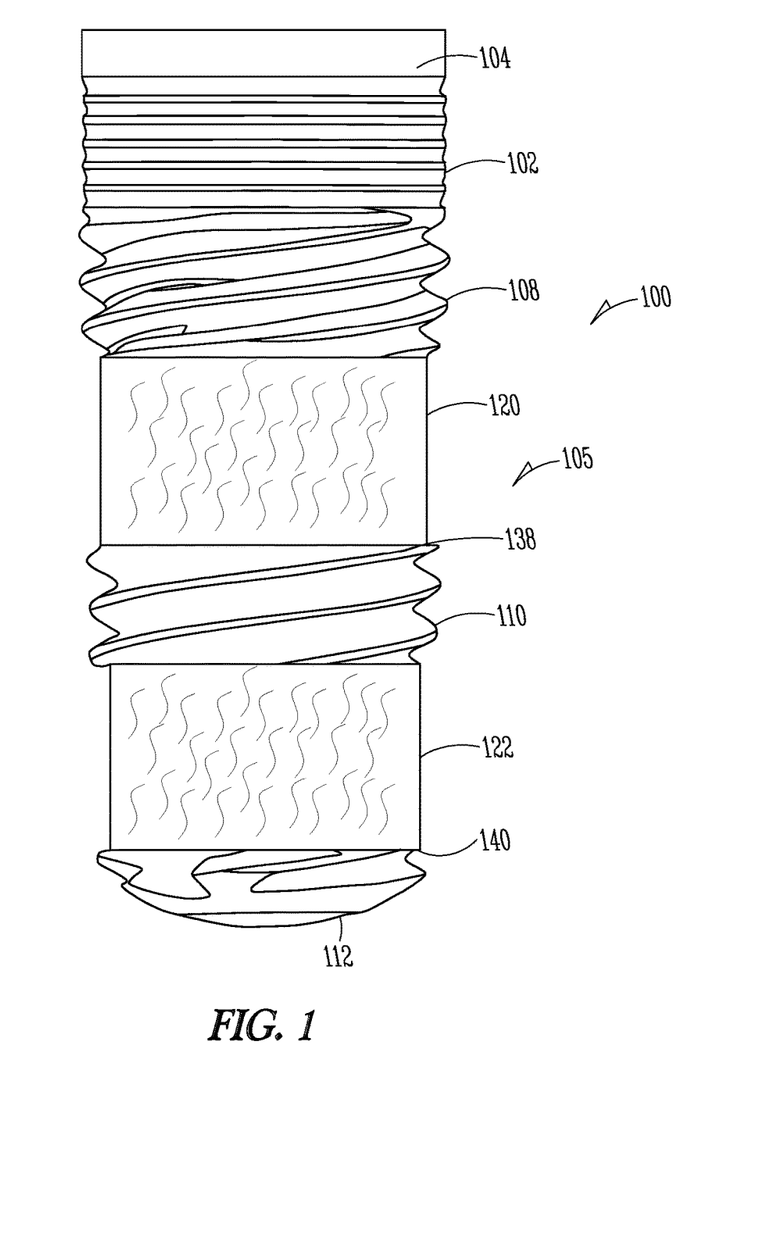
FIG. 1 shows a side view of a dental implant.
Figure 2:
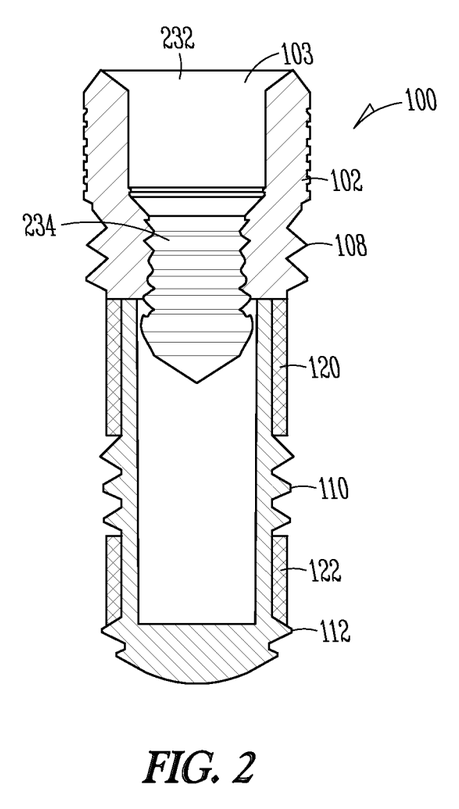
FIG. 2 shows a cross-section view of the dental implant of FIG. 1.

FIG. 1 shows a side view of an example of a dental implant 100, and FIG. 2 shows a cross-section view of the dental implant 100. The dental implant 100 can include a core 102 that can have a head portion 104 that can include an abutment interface 103, and a stem portion 105 extending from the head portion 104. The stem portion 105 can include a first, coronal threaded section 108, an intermediate threaded section 110, and a third, apical threaded section 112; each of these threaded sections can be separated from adjacent threaded section(s) by a non-threaded region. The core 102 can be made of a suitable biocompatible material, such as titanium. The threaded sections 108, 110, and 112 can have a tapered structure such that apical threaded section 112 has a smaller diameter than threaded sections 108 and 110, and intermediate threaded section 110 has a smaller diameter than coronal threaded section 108. The threaded sections 108, 110, and 112 can be non-porous. An internal hex 232 and an internally threaded bore 234 can be provided, such as for attaching a dental abutment. The core 102 can be solid or have at least a partially hollow structure.

The dental implant 100 can include a first porous section 120 and a second porous section 122 located along the stem portion 105, forming a stratified structure. The intermediate threaded section 110 of the stem portion 105 can separate the first porous section 120 from the second porous section 122, such that the first porous section 120 can be located towards the coronal end of the dental implant 100 and the second porous section 122 can be located towards the apical end of the dental implant 100.

The first and second porous sections 120, 122 can include or can be formed of a porous material, such a porous metallic material, such as porous tantalum. The first and second porous sections 120, 122 can include porous metallic sleeves, such as porous tantalum sleeves that can be disposed along the length of the stem portion 105.

For example, the first and second porous sections 120, 122 can be formed of highly porous biomaterial useful as a bone substitute and/or cell and tissue receptive material. An example of such a material can be produced using Trabecular Metal® technology generally available from Zimmer, Inc., of Warsaw, Ind. Trabecular Metal® is a trademark of Zimmer Technology, Inc. Such a material can be formed from a reticulated vitreous carbon foam substrate, which can be infiltrated and coated with a biocompatible metal, such as tantalum, etc., such as using a chemical vapor deposition ("CVD") process, such as in the manner disclosed in detail in U.S. Pat. No. 5,282,861, the disclosure of which is incorporated herein by reference. One or more other metals such as niobium, titanium, or one or more alloys of tantalum and niobium with each other or with one or more other metals can also be used.

The porous tantalum structure of the porous sections 120, 122 can include a large plurality of ligaments defining open spaces therebetween, with an individual ligament generally including a carbon core covered by a thin film of metal, such as tantalum, for example. The open spaces between ligaments can form a matrix of continuous channels, such that growth of cancellous bone through the porous tantalum structure can be uninhibited. The porous tantalum can include up to 75%-85% or more void space therein. Porous tantalum can provide a lightweight, strong porous structure, which can be substantially uniform and consistent in composition, and can closely resemble the structure of natural cancellous bone, and thereby can provide a matrix into which cancellous bone can grow, such as to anchor the dental implant 100 into the surrounding bone of a patient's jaw.

The porous tantalum structure can be made in a density that can be selected from variety of available densities, such as to selectively tailor the structure for a particular application. In particular, such as discussed in the above-incorporated U.S. Pat. No. 5,282,861, the porous tantalum can be fabricated to a desired porosity and pore size, and can thus be matched with the surrounding natural bone, such as to provide a matrix that can facilitate bone ingrowth and mineralization.

As the dental implant 100 is being inserted into a patient's jaw, the first and second porous sections 120, 122 can be considered to be "dead zones" where the dental clinician cannot feel what the surrounding bone feels like. There is a tactile difference between the porous sections 120, 122 and the threaded sections 110, 112, and 108, during insertion of the dental implant 100. Dental clinicians may rely on tactile resistance during implant placement, such as to determine bone quality or to determine the speed of restoration. Here, the dental implant 100 allows for multiple tissue regions to be evaluated as the dental implant 100 is being placed, due to the tactile resistance of threaded sections 108, 110, 112. This can give the clinician additional information, such as regarding bone quality.

The dental implant 100 can reduce the continuous distance of the collective dead zone of the porous sections 120, 122, such as by using the intermediate threaded section 110 between the porous sections 120, 122. This structure can also help during implantation because a long continuous dead zone creates a section of the implant that cannot be effectively driven or backed out of the osteotomy. Should there be a need to reposition or re-drill the osteotomy, the clinician will be hindered from withdrawing such an implant. In contrast, in the present implant 100, when the porous sections 120 or 122 are contacting bone, the intermediate threaded section 110 can allow the clinician to agitate or otherwise manipulate the dental implant 100, such as to reengage the threaded section 110 into bone. This can help allow the clinician to resume control during the implantation. The present implant 100 can improve surgical control and initial stability of the implant 100 while providing sufficient porous volume from porous sections 120 and 122 to allow for secondary bone apposition.

The configuration of the implant 100 can also help improve mechanical and biological function of the implant 100. The implant 100 can be configured to provide an improved method for improving primary and secondary implant fixation, such as by increasing surgical control during placement, and such as by minimizing the sensitivity of prior implants to variations in bone density.

In an example, the first porous section 120 can have a greater diameter than the second porous section 122. Each of the first porous section 120 and the second porous section 122 include an apical edge (e.g., a scraping edge) 138 and 140, respectively. The greater diameter of the first porous section 120 can allow its leading apical edge 138 to engage the osteotomy wall. The leading apical edges 138 and 140 can generate bone particulate as the implant is screwed into the osteotomy. The bone particulate can become entangled with or embedded within the porous material of porous sections 120 and 122. These entangled or embedded bone fragments can function similarly to a bone grafting material, and can help enhance secondary tissue ingrowth. However, if a single porous section were used for implant 100, the bone fragments may not reach the coronal aspect of the implant because they may have been exhausted and fully embedded at the apical end of the single porous section. The present implant 100, with two separate porous sections 120, 122 that can have different diameters, can allow the apical edge 138 of the first porous section 120 to develop bone fragments for the porous section 120, which can thus help promote resulting in faster secondary bone ingrowth.

Moreover, by having the first porous section 120 with a greater diameter than the second porous section 122, the primary implant stability can be increased, because the offset diameters of the first and section porous section 120, 122 can allow for increased tissue compression of the implant within the osteotomy.

In an example, the implant 100 can be formed as a layered structure. In such an example, a first section of the core 102 that is above (e.g., more proximal than) the intermediate threaded section 110 can be provided. The porous section 120 can be slipped over the stem and secured to the core 102 in a suitable manner, such as via cement or by sintering the porous section 120 to the core 102, for example. The intermediate threaded section 110, with its stem, can then be attached to the upper portion of the implant, such as by welding, for example. The second porous section 122 can then be slipped over the stem and attached to the core 102, such as discussed above. Then, the lower threaded section can be attached to the bottom of the stem to complete the implant 100.

In an example, the porous section 120, 122 can be attached to the core 102 in a manner wherein, after osseointegration of porous sections 120, 122 into the surrounding bone, the core 102 can be slightly movable relative to the porous sections 120, 122, such as to dissipate mastication or other forces imposed upon the implant 100. For example, the porous sections 120, 122 can be secured to the core 102, such as via an adhesive material that is slightly compressible, such that when mastication or other forces are imposed upon the head portion of the implant 100 via the prosthesis and abutment, the head portion and/or stem portion of the core 102 of the implant 100 can move slightly relative to the porous sections 120, 122.

Figure 3:
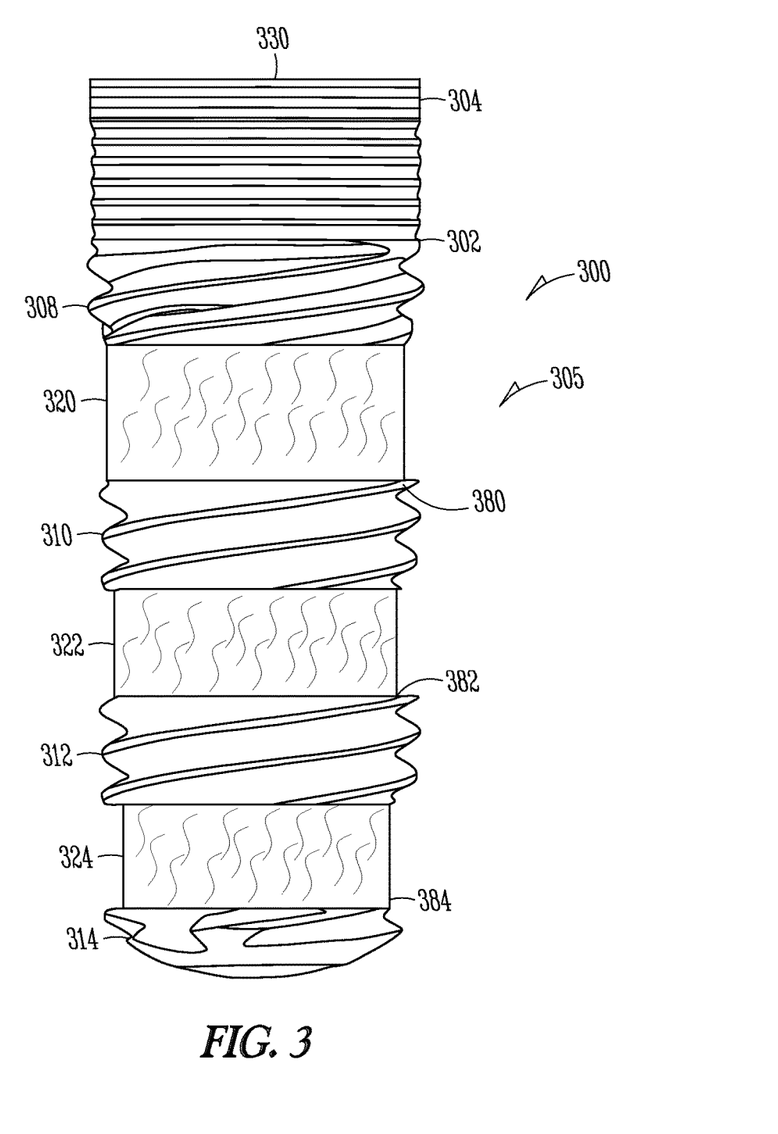
FIG. 3 shows a side view of a dental implant.

FIG. 3 shows a side view of an example of a dental implant 300. The dental implant 300 can be similar to the dental implant 100 described above, but in this case, the dental implant 300 can include an additional porous section.

The dental implant 300 can generally include a core 302 that can have a head portion 304, such as can include an abutment interface 330, and a stem portion 305, such as extending from the head portion 304. The stem portion 305 can include a first, coronal threaded section 308, a first intermediate threaded section 310, a second intermediate threaded section 312, and an apical threaded section 314. The core 302 can be made of a suitable biocompatible material, such as titanium. The threaded sections 308, 310, 312, and 314 can have a tapered structure, e.g., such that the apical threaded section 314 can have a smaller diameter than the threaded sections 308, 310, and 312, and the second intermediate threaded section 312 can have a smaller diameter than the coronal threaded section 308 and the first intermediate threaded section 310, and the first intermediate threaded section 310 can have a smaller diameter than coronal threaded section 308. The threaded sections 308, 310, 312, and 314 can be non-porous. The implant 300 can further include an internal hex and an internally threaded bore, such as for attaching a dental abutment, such as discussed above for implant 100.

The dental implant 300 can include a first porous section 320, a second porous section 322, and a third porous section 324 located along the stem portion 305. The first intermediate threaded section 310 of the stem portion 305 separates the first porous section 320 from the second porous section 322, and the second intermediate threaded section 312 separates the second porous section 322 from the third porous section 324. Thus, the first porous section 320 can be located toward the coronal end of the dental implant 300, the second porous section can be located at an intermediate area of the implant 300, and the third porous section 324 can be located toward the apical end of the dental implant 300.

In an example, the first porous section 320 can have a greater diameter than the second porous section 322, and the second porous section 322 can have a greater diameter than third porous section 324. Each of the first porous section 320, the second porous section 322, and the third porous section 324 can include an apical edge 380, 382, and 384, respectively. As discussed above, the relatively greater sizes of each porous section 320, 322, and 324, proceeding from the apical toward the coronal end of the implant 300, can allow each of the leading apical edges 384, 382, and 380 to engage the osteotomy wall. As discussed, this can help improve retention of bone particulate along the entire length of the implant 300. Further, the primary implant stability can be increased since the offset diameters of the first, section, and third porous sections 320, 322, and 324 allow for successively increased tissue compression of the implant within the osteotomy.

In other embodiments, four or more porous sections can be provided for an implant, such as discussed herein.

Figure 4:
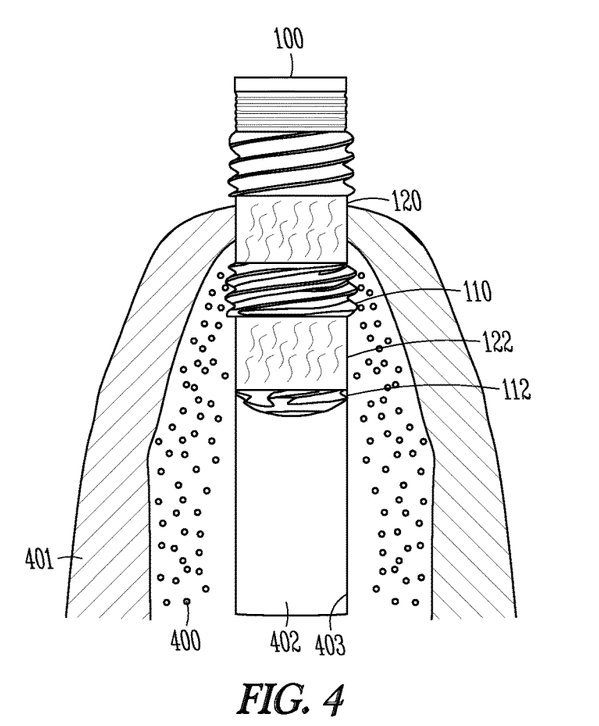
FIG. 4 shows a side view of the dental implant of FIG. 1 during implantation.
Figure 5:
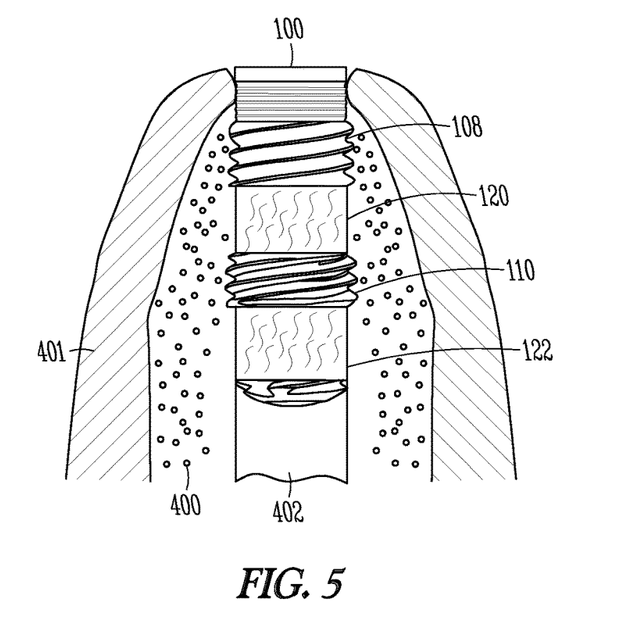
FIG. 5 shows the dental implant of FIG. 1 after being implanted.

FIGS. 4 and 5 show an example of the implant 100 being implanted, with FIG. 4 showing a side view of the dental implant 100 during implantation and FIG. 5 showing the dental implant 100 after being implanted.

Here, a mouth can include a gingava 401, a bone 400 and an osteotomy 402 bored into the bone 400 to receive the implant 100. A dental clinician can insert the dental implant 100 into the osteotomy such that the first threaded apical section 112 contacts an osteotomy wall 403. As the dental implant 100 is further implanted, the apical porous section 122 contacts the osteotomy wall, then the intermediate threaded section 110 contacts the osteotomy wall, and then the coronal porous section 120 contacts the osteotomy wall. As discussed, the porous section 120 can have a larger diameter than the porous section 122, such that each leading apical edge of each of the porous sections 120, 122 can produce bone particulate during the implantation, which can then become entangled with or embedded in the porous material, such as to enhance the grafting process.

Thereafter, a cap can be fitted onto the implant 100, such as to close the abutment coupling structure of the implant 100, and the gingiva can be sutured over the implant. In a second stage of the procedure, following osseointegration, the dental clinician can reopen the gingiva at the implant site, and can secure an abutment and, optionally, a temporary prosthesis or temporary healing member, to the implant 100. Then, a suitable permanent prosthesis or crown can be fashioned, such as from one or more impressions taken of the abutment and the surrounding gingival tissue and dentition. Then, the temporary prosthesis or healing member can be removed and replaced with the permanent prosthesis, which can be attached to the abutment, such as with cement or with a fastener, for example.

In some examples, the stratified structure of the described implant can be incorporated into other implants such as spinal implants.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. An implant comprising:
  a core, having a head portion including an abutment interface adapted for receiving a dental abutment and a stem portion extending from the head portion, the stem portion including a coronal threaded section, an intermediate threaded section, and an apical threaded section;
  a first porous section located along the stem portion, the first porous section having an exterior non-threaded surface arranged to contact bone, the exterior non-threaded surface extended entirely around a cross-sectional circumference of the first porous section; and
  a second porous section located along the stem portion, the second porous section being non-contiguous with the first porous section and having an exterior non-threaded surface arranged to contact bone, the second exterior non-threaded surface extending entirely around a cross sectional circumference of the second porous section, wherein the implant has a layered structure such that the intermediate threaded section of the stem separates the first porous section from the second porous section and the first porous section is between the coronal threaded section and the intermediate threaded section, and the second porous section is between the intermediate threaded section and the apical threaded section.

2. The implant of claim 1, wherein the first non-threaded porous section and the second non-threaded porous section, respectively, are first and second porous sleeves disposed around the stem portion.

3. The implant of claim 2, wherein the first and second porous sleeves each has an exterior non-threaded surface arranged to contact bone.

4. The implant of claim 3, wherein the first and second porous sleeves are porous tantalum, porous titanium, or porous niobium sleeves.

5. The implant of claim 1, wherein the first non-threaded porous section has a greater external diameter than an external diameter of the second non-threaded porous section.

6. The implant of claim 1, wherein the first non-threaded porous section is located toward a coronal end of the implant and the second non-threaded porous section is located toward an apical end of the implant.

7. The implant of claim 1, including a third porous section located along the stem portion.

8. The implant of claim 7, wherein the stem includes a second intermediate threaded section separate from the intermediate threaded section and the second intermediate threaded section separates the third porous section from the second non-threaded porous section.

9. The implant of claim 1, wherein the intermediate threaded section is nonporous.

10. The implant of claim 1, wherein the first non-threaded porous section includes a porous tantalum sleeve disposed around the stem portion and the second non-threaded porous section includes a porous tantalum sleeve disposed around the stem portion.

11. The implant of claim 1, wherein an entirety of each of the first and second non-threaded porous sections is non-threaded.

12. An implant comprising:
a core, having a head portion, including an abutment interface, and a stem portion, extending from the head portion, the stem portion including a first, coronal threaded section, an intermediate threaded section, and a third, apical threaded section;
a first porous metallic sleeve disposed around the stem portion, wherein the first porous metallic sleeve includes a non-threaded exterior surface arranged to contact bone, the non-threaded exterior surface extending entirely around a circumference of the first porous metallic sleeve;
a second porous metallic sleeve disposed around the stem portion, the second porous metallic sleeve being non-contiguous with the first porous metallic sleeve and including a non-threaded exterior surface arranged to contact bone, the non-threaded exterior surface extending entirely around a circumference of the second porous metallic sleeve, wherein the implant has a layered structure such that the intermediate threaded section of the stem portion separates the first porous metallic sleeve from the second porous metallic sleeve and the first porous metallic sleeve is between the coronal threaded section and the intermediate threaded section, and the second porous metallic sleeve is between the intermediate threaded section and the apical threaded section; and
wherein the first porous metallic sleeve is located toward a coronal end of the implant and the second porous metallic sleeve is located toward an apical end of the implant.

13. The implant of claim 12, wherein the first porous metallic sleeve has a greater diameter than the second porous metallic sleeve.

14. The implant of claim 12, including a third porous metallic sleeve disposed. around the stem portion.

15. The implant of claim 14, wherein the stem portion includes a second, intermediate threaded section separate from the intermediate threaded section, and wherein the second intermediate threaded section separates the third porous metallic sleeve from the second. porous metallic sleeve.

16. The implant of claim 12, wherein the first, coronal threaded section, the intermediate threaded section, and the third, apical threaded section are non-porous.

17. The implant of claim 12, wherein the first porous metallic sleeve includes a porous tantalum sleeve and the second porous metallic sleeve includes a porous tantalum sleeve.

18. The implant of claim 12, wherein the first, coronal threaded section has a greater diameter than the intermediate threaded section, and the intermediate threaded section has a greater diameter than the third, apical threaded section.

19. The implant of claim 12, wherein the first and second porous metallic sleeves include porous tantalum, porous titanium, or porous niobium sleeves.

20. The implant of claim 12, wherein an entirety of each of the exterior surfaces of the second porous metallic sleeves is non-threaded.

21. A method comprising:
inserting a dental implant into a mouth such that a first threaded apical section on a stem of the dental implant contacts an osteotomy wall formed in a patient's mandible or maxilla;
further inserting the dental implant such that an apical porous section contacts the osteotomy wall, the apical porous section having a non-threaded exterior surface, the non-threaded exterior surface extending the entirely around circumference of the apical porous section;
further inserting the implant such that an intermediate threaded section on the stem of the implant contacts the osteotomy wall;
further inserting the implant such that a coronal porous section contacts the osteotomy wall, the coronal porous section having a non-threaded exterior surface, the non-threaded exterior surface extending entirely around a circumference of the coronal porous section; and
further inserting the implant such that a coronal threaded section on the stem of the implant contacts the osteotomy wall;
wherein the coronal porous section is noncontiguous with the apical porous section and the dental implant has a layered structure such that the intermediate threaded section separates the coronal porous section from the apical porous section and the coronal porous section is between the coronal threaded section and the intermediate threaded section, and the apical porous section is between the intermediate threaded section and the apical threaded section.

22. The method of claim 21, wherein the apical porous section has a smaller diameter than the coronal porous section.

23. The method of claim 21, wherein the apical porous section and the corona porous section are non-threaded.

24. The method of claim 23, wherein an entirety each of the apical and coronal porous sections are non-threaded.

25. The method of claim 21, wherein the intermediate threaded section is non-porous.

* * * * *

UNITED STATES PATENT AND TRADEMARK OFFICE
CERTIFICATE OF CORRECTION

PATENT NO. : 9,700,387 B2
APPLICATION NO. : 13/912740
DATED : July 11, 2017
INVENTOR(S) : Sanchez et al.

Page 1 of 1

It is certified that error appears in the above-identified patent and that said Letters Patent is hereby corrected as shown below:

In the Claims

In Column 8, Line 17, in Claim 1, delete "extended" and insert --extending-- therefor In Column 9, Line 36, in Claim 14, delete "disposed." and insert --disposed-- therefor In Column 9, Line 41, in Claim 15, delete "second." and insert --second-- therefor

In Column 10, Line 7, in Claim 20, after "the", insert --first and-- (2nd Occurrence)

In Column 10, Line 18, in Claim 21, after "extending", delete "the"

In Column 10, Line 19, in Claim 21, after "around", insert --a--

In Column 10, Line 46, in Claim 23, delete "corona" and insert --coronal-- therefor Signed and Sealed this
Nineteenth Day of March, 2019

Andrei Iancu
*Director of the United States Patent and Trademark Office*